United States Patent [19]

Robertson

[11] Patent Number: 4,669,478
[45] Date of Patent: Jun. 2, 1987

[54] DEVICE FOR DIAGNOSING AND RELIEVING FEMALE INCONTINENCE

[76] Inventor: Jack R. Robertson, 1451 Refugio Rd., Santa Ynez, Calif. 93460

[21] Appl. No.: 714,268

[22] Filed: Mar. 21, 1985

[51] Int. Cl.⁴ ............................................... A61B 5/00
[52] U.S. Cl. ..................................... 128/630; 128/344
[58] Field of Search ............... 128/630, 778, 341, 343, 128/344

[56] References Cited

U.S. PATENT DOCUMENTS

| | | | |
|---|---|---|---|
| 2,499,045 | 8/1948 | Walker et al. | 128/344 |
| 3,646,929 | 3/1972 | Bonnar | 128/344 |
| 3,841,304 | 10/1974 | Jones | 128/344 |
| 4,137,922 | 2/1979 | Leininger et al. | 128/344 |

Primary Examiner—Kyle L. Howell
Assistant Examiner—Randy Citrin
Attorney, Agent, or Firm—Romney Golant Martin Seldon & Ashen

[57] ABSTRACT

An inflatable elongate pessary fits into and longitudinally distends the patient's vagina and with it the urethra. An indentation near the proximal end of the pessary receives the patient's servix so that the pessary can extend into and distend the most proximal region behind the cervix. Preferably a lateral enlargement near the distal end of the pessary aids in supporting the pessary above the levator ani sling. The pessary moves the bladder neck and the proximal portion of the urethra toward normal positions above the abdominal wall. The pessary includes a flexible airtight chamber, and a valve and fitting that are operable from outside the vagina while the pessary is inside. The fitting is accessible from the outside for attachment of a source of compressed gas, while the pessary is in the vagina. Within the pessary is preferably a longitudinal cavity, open at the distal end of the pessary but extending near the proximal end; the patient can insert a finger into this cavity to push the pessary all the way up into the vagina.

37 Claims, 11 Drawing Figures

DEVICE FOR DIAGNOSING AND RELIEVING FEMALE INCONTINENCE

BACKGROUND

1. Field of the Invention

This invention relates generally to diagnostic and therapeutic apparatus and methods in gynecology, and more particularly to diagnosing and relieving the symptoms of incontinence in women.

2. Prior Art (a) Causes of Incontinence—Inability to deter the flow of urine from the bladder is a common phenomenon in women, particularly older women. Such inability to contain urine is termed "incontinence." Roughly half of elderly women are incontinent.

An incontinent woman usually has an adequate reservoir (the bladder) for urine, but the biological "valve" is for one or another reason inadequate to prevent discharge of urine. The "valve" that normally performs this function is the urethra—the duct through which the bladder is normally emptied during urination—in conjunction with the muscle or sphincter that surrounds the urethra.

The most frequently encountered causes of incontinence in women may be classified as pathogenic, anatomical and neurological. Before incontinence in a particular woman is treated, its cause must be ascertained. Not only is appropriate treatment for each kind of incontinence ineffective against other kinds of incontinence, but in some instances appropriate treatment for one type is counterproductive with respect to other types.

Incontinence that is pathogenic—caused by infection—is readily identified in ways that are outside the primary scope of my invention. (As will be seen, my invention is compatible with procedures for checking the possibilities of pathogenic incontinence.)

Anatomical and neurological incontinence, however, are readily confused by diagnosticians.

Historically, distinguishing between them has been attempted by direct observations, and very recently it has been accomplished by sophisticated instrumentation. In addition, my copending patent application Ser. No. 661,087 describes an inexpensive diagnostic apparatus that is extremely effective in facilitating the earlier, direct form of observation. All three of these systems will be described below. Unfortunately the earlier forms of direct observation are subject to several obstacles and inaccuracies, whereas the instrumentation is subject to such extremely high cost as to be accessible only to medical centers (as distinct from individual clinicians)—and even so is not free from certain inaccuracies and other disadvantages.

The diagnostic aid described in my copending application is superior to the earlier forms of direct observation and the instrumentation, but it is somewhat more time consuming than the present invention. It is also limited to diagnostic use, whereas the present invention provides symptomatic relief as well.

To understand the shortcomings of these other technologies it is necessary to understand the behavior and causes of anatomical and neurological incontinence. Both of these types appear in response to bodily stress, and particularly as reactions to a relatively abrupt increase in pressure within the abdomen.

(Traditionally the anatomical type of incontinence has been identified as "genuine stress incontinence" though both of these two types are in fact triggered by stress, and it may therefore be more accurate to describe both as, at least, "stress incontinence.")

A cough, sneeze or laugh is often the stimulus for such a pressure increase, but in more advanced stages of incontinence the patient may be unable to contain her urine even against pressure increases such as are incurred through light exercise: lifting, bending down, running, or even merely walking. Since these sorts of stress are basic to everyday living and use of the body, it will be apparent that advanced stress incontinence is virtually debilitating. Patients in which such conditions are untreated must resort to adult-size diapers or other cumbersome, relatively unsanitary, and potentially embarrassing appliances.

Stress-induced pressure increases, in normal women as well as women suffering from both types of stress incontinence, are transmitted to the bladder (though by different mechanisms), causing the pressure within the bladder to rise. In normal women, however, the pressure incurred by coughing, exercise, and so forth is exceeded by the pressure within the urethra.

When normal individuals are not urinating, the urethra is held closed by voluntarily controlled musculature (the sphincter surrounding the urethra), with the aid of surrounding anatomical structures. This musculature and other anatomical features produce a pressure within the urethra that exceeds any pressure ordinarily produced by stresses (pressures) transmitted to or arising in the bladder.

The higher pressure within the urethra stands off the liquid stored in the bladder, preventing the liquid from being discharged through the urethra and thereby out of the body.

Another important factor operates in aid of the muscles and other features in the normal woman: both the bladder and the urethra are subjected in common to various pressures within the abdomen. Thus for example, pressure arising from a cough is applied to both the bladder and the urethra. With regard to the urethra, the pressure under discussion here is lateral or radial, pushing inwardly from the sides of the urethra and so tending to hold the urethra closed. Consequently the tendency of any particular pressure to squeeze fluid out of the bladder is directly counteracted by the tendency of that selfsame pressure to squeeze the urethra shut.

There are primarily two ways in which this normal control system can fail: (1) the muscles and the structure that normally hold the urethra closed can become weak, and (2) the body can malfunction in such a way as to amplify the pressure increase within the bladder. In either of these abnormal situations, the pressure within the urethra is insufficient to stand off the pressure in the bladder—and urine is forced outward from the bladder through the patient's urethra.

The first of these two kinds of failure is due to three interrelated anatomical weaknesses: the sphincter muscle that squeezes the urethra closed is no longer able to exert the normal amount of force; the bladder opening at the top of the urethra, and the inner (or proximal, in medical terminology) end of the urethra have lost their support; and the musculature structure around the base of the urethra and vagina has lost its tone. (This structure is the levator ani sling—a hammock-shaped musculature which extends across and closes off the abdomen, except for the vaginal, urethral and anal orifices.) These weakenings probably occur either as a result of childbirth or as part of the general deterioration of bodily structures with advancing age, or both.

The inner end of the urethra, in any event, is broadened—practically becoming part of the bladder, so that the urethra itself is effectively foreshortened. The urethra also undergoes "prolapse"—it falls down or slips from its normal position—and the outer end of the urethra is virtually buried in the levator ani sling. It is this part of the urethra that is surrounded by the urethral sphincter.

The resulting phenomena may be viewed in a relatively mechanical way: a sudden increase in pressure within the abdomen (as with a cough) is transmitted to the bladder, but not to the urethra. The urethra in its prolapsed position is shielded by the surrounding levator ani sling from the pressure within the abdomen, and bladder pressure becomes greater than urethral pressure. In addition, the urethral sphincter is relatively ineffective in its function as a valve. Due to the foreshortening of the urethra, the full weight of the contents of the bladder is brought to bear more directly than normal upon this already-handicapped control system. Due to these factors in combination, urine is forced outwardly through the urethra.

Anatomical incontinence thus arises from selective application of intraabdominal pressure—application to the bladder but not to the urethra—compounded by weakened sphincter action and a downwardly displaced hydraulic loading. This is known as "genuine stress incontinence." It can be treated surgically, or to a generally unsatisfactory degree by prosthetic therapy, but not by administration of medicines. The prosthetic approach will be discussed in some detail later.

Surgical procedures suspend the vagina and thereby pull upwardly on the urethra to return the urethra to the region of normal intraabdominal pressure, above the levator ani sling. The rationale is to reequalize the application of intraabdominal pressure. Approximately one hundred fifty different operative procedures have been devised. Certain of these procedures are recognized as effective; however, surgery has several limitations.

Surgery is always a relatively drastic and expensive alternative. It may be entirely contraindicated for the very elderly or others whose general condition is frail. Moreover, surgery is to be avoided if the patient's etiology is not "anatomical incontinence," since surgery can often aggravate incontinence arising from other causes. Finally, there is often a protracted delay while the patient awaits a surgical date; during this time the patient requires some relief.

The second of the two kinds of failure enumerated above, the amplification of the stress-induced pressure increase, can occur in a woman whose urethral pressure is ample to withstand the abdominal pressure increase that is directly associated with a cough, sneeze, laugh, or even vigorous exercise. In this second kind of incontinence, however, the increased pressure within the bladder triggers nerve signals, and these nerve signals abnormally stimulate the bladder to contract. The contraction of the bladder in turn raises the pressure within the bladder very severely— to a level considerably greater than that produced directly by the stress.

The nerve signals triggered by the original pressure increase in the bladder may travel to the brain, causing return signals to the bladder along nerve paths normally used by the patient to squeeze the bladder and thereby help expel urine from the bladder. It is also possible that the nerve signals cause a more-localized chain reaction of spasms that eventually return to squeeze the bladder. Whatever the specific mechanism, this type of incontinence is characterized by a time delay of at least three to five seconds, and sometimes as long as fifteen to twenty seconds, between the originating stress and the responding contraction and discharge. In addition to the difference in timing, this type of incontinence also is usually characterized by a greater volume of discharge.

This type of stress incontinence is often called "bladder instability." It can be treated by administration of medicines, but not by surgery or prosthetic therapy. In fact, attempts to correct it surgically often result in aggravating the condition.

(b) Diagnostics: the "Stress Test"—A historically common method of determining which type of incontinence a woman has is the so-called "stress test" introduced by Doctors Bonney, Marshall and Reid. In the stress test the patient's bladder is filled with fluid (often a quarter of a liter of salt solution) and she is asked to cough. If fluid is discharged from her urethra immediately, the patient is diagnosed as suffering from "genuine stress incontinence" and requiring surgery, whereas if there is a delay the patient is diagnosed as having "bladder instability" and requiring medication. The test of course relies upon the difference in timing between the two kinds of reaction. Unfortunately this so-called "stress test" is flawed in several ways.

First, about half of incontinent women are continent when lying down. This fact results from the force of gravity on fluid in the bladder and on other bodily organs near the bladder. In a standing patient the proximal end of the urethra is essentially at the bottom of the pool of fluid in the bladder, and gravity adds substantially to the stress-induced pressure at the proximal end of the urethra. Furthermore, the weight of organs that are above the bladder tends to be applied to the bladder when the patient stands.

When the patient reclines, however, the rotation of the bladder and surrounding structures places the proximal end of the urethra much closer to the upper surface of the fluid in the bladder, or even above the upper surface, so that gravity makes no substantial addition to the stress-induced pressure at the proximal end of the urethra. At the same time there are fewer organs disposed to press upon the bladder when the patient reclines.

Hence the test must be conducted with the patient standing. Unfortunately, however, it is very undesirable to perform such a test with the patient standing. The standing patient will not generally be able to spread her legs sufficiently to allow the diagnostician a clear view of the distal (outer) end of the uretha. Consequently the diagnostician usually inserts her or his fingers within the patient's labia (the folds of flesh covering the vaginal outlet) to determine when that area is wetted by discharge of fluid. Under such conditions it is extremely difficult to accurately determine the timing of the discharge relative to the stress, especially considering that in some patients suffering from bladder instability the time delay is only three seconds.

Secondly, in a setting such a doctor's office the patient is often anxious. This often causes the voluntary sphincter of the uretha to go into involuntary spasm (that is, to squeeze the uretha shut), which obstructs the flow of fluid from the bladder. It has been shown that one-third or more of incontinent women may be unsable to demonstrate incontinence under these circumstances.

After leaving the doctor, however, the patient may again become incontinent.

This problem is aggravated by the fact that the patient must stand during the test, essentially confronting the doctor, with the doctor's fingers placed within the patient's labia. This confrontation accentuates the patient's realization that any fluid lost will wet the doctor's fingers, and such behaviour of course contradicts all normal social schooling. As a result, in addition to the involuntary anxiety spasm discussed in the preceding paragraph, many patients may actually consciously squeeze the urethral sphincter more forcefully than they may normally squeeze during coughing, sneezing, exercising, etc.—thereby defeating the test.

Thirdly, many women have relatively large labia, which can act as a dam to discharge of fluid from the urethra. This effect makes it very difficult to determine whether fluid from the bladder is lost immediately or after a delay.

Fourthly, many women are obese, and the compound obstructions formed by rolls of flesh and folds of skin at the thighs of an obese patient similarly dam the fluid emerging from the urethra. The timing determination is accordingly impeded.

Fifthly, in any observation of biological phenomena there is a certain amount of imprecision. Diagnosticians may find that a discharge occurs with a seeming delay of one or two seconds, which does not correspond neatly to either category of stress incontinence. Similarly diagnosticians may find that some discharge occurs immediately after stress, and that an additional discharge "seems" to occur later. It must be realized that some women suffer from both types of incontinence, which would account for a dual discharge, but it is extremely difficult to determine reliably that a second discharge has occurred after the labia and the diagnostician's fingers are already wetted.

(c) Diagnostics: Other Direct Observations—Partly as a result of the difficulties just described, diagnosticians usually perform other tests to gather additional information on the patient's anatomical condition. In particular, one common test—familiarly known as the "Q-tip test"—involves inserting a "Q-tip" cotton swab partway into the urethra, while the patient is lying on her back in the customary pelvic-examination position, and instructing the patient to bear down (as in defecation). In these circumstances the swab initially is generally horizontal, and deflects upward when the patient bears down.

In a normal patient the upward deflection does not exceed roughly thirty degrees. In the abnormal anatomical condition that gives rise to so-called "genuine stress incontinence," however, the upward deflection can approach ninety degrees. Since many diagnosticians are accustomed to including this test in their "work up," it is desirable to ensure that any new procedure proposed is compatible with—or, preferably, facilitates—some version of the "Q-tip test."

Similarly, it is generally routine to take a sample of urine directly from the patient's bladder. Such a sample is helpful in checking for pathogenic conditions, since it is less likely than an excreted sample to be contaminated by chance unsanitary conditions within or just outside the patient's labia. Consequently in any new procedure the obtaining of such a sample should be facilitated.

(d) Diagnostics: Modern Instrumentation—The ambiguities in the now-classical "stress test" have led to introduction of electronic instrumentation for determining essure relationships between the bladder and the proximal end of the urethra.

Such instrumentation generally consists of (1) a first pressure sensor that is inserted entirely through the urethra into the bladder, to sense the pressure within that organ; (2) a second pressure sensor that is inserted partway through the urethra, to sense the pressure along that duct, and (3) electronics and display devices for determining and recording those two pressures as they change with time, and in some instruments for also determining and recording certain relationships between those pressures.

The pressure sensors used may be of two different types. First, a pressure sensor may consist of (a) a small transducer, positionable within the bladder or urethra, that controls an electrical resistance or an electrical voltage source—together with (b) electrical leads for directing to the exterior of the body electrical signals related to the sensed pressure, and (c) a rod or the like for inserting the transducers and leads into position, and holding them in position, for measurement.

The other type of pressure sensor may consist of (a) a pair of tubes inserted into the bladder and urethra respectively, and (b) pressure-measurement devices attached to the ends of the tubes that are outside the body, to measure the pressure transmitted through the tubes while the tubes are held in position. With this type of sensor, the tubes are usually provided in the form of a single tube structure with parallel channels within it, and separate openings spaced along the tube near its proximal end.

In use of these instruments, the pressure sensors (of either type) are inserted together into the urethra while the patient reclines in the usual pelvic-examination position. One sensor is advanced approximately two to three inches forward of the other sensor, while the instrument operator observes the changing pressure readouts from the instrument. When the readout from the forward or proximal sensor decreases (indicating that the sensor has passed from the urethra into the bladder) but the readout from the rearward or distal sensor remains higher (indicating that this sensor has not yet reached the bladder), the insertion is stopped and data are taken.

In one very expensive unit, the instrument operator advances the sensor pair into the urethra and bladder, and then the apparatus (rather than the operator) automatically withdraws the catheter at a regular velocity, while measuring and recording the pressure relationships between bladder and urethra.

In other parts of the diagnosis the patient is instructed to cough, laugh, exercise, or otherwise incur abdominal stress, and the sensor measurements are recorded as they respond to the stress.

Instruments of this type are operationally preferable to the "stress test." The sensors can be emplaced while the patient is lying down and are relatively unintrusive, making insertion fairly easy.

Because the apparatus is very sensitive and relies upon pressure measurements rather than actual discharge of urine, it appears from the literature that for some patients the entire test can be successfully (that is, accurately) conducted while the patient reclines.

Yet modern instrumentation for stress-incontinence diagnosis is unsatisfactory in at least four ways.

First, there remains a very large fraction of the population of incontinent patients whose incontinence is masked by the patients' lying down.

Secondly, the equipment is prohibitively expensive for use by individual clinicians. The cost for one operational device ranges roughly from $7,000 to $50,000, depending upon the degree of automaticity desired. Modern medical philosophy, however, for very good reasons favors acquiring as much information as possible in the doctor's office, rather than in the hospital or large-scale medical center.

Although this instrumentation has found an effective market among high-volume diagnostic laboratories such as those found in medical centers, even as evaluated by these facilities such an instrument is inordinately expensive.

Thirdly, its operation is surprisingly time-consuming, requiring generally an hour to an hour and a half for full diagnosis of each patient—though only a part of this time is occupied by the actual testing. This inordinate consumption of time is wearing on the patient, and also is expensive in terms of laboratory personnel.

Fourthly, many a patient (particularly among the elderly) finds it personally degrading or offensive to have her genital region connected to a machine. This is particularly true if a cost-conscious technician, having set up the test, goes off to tend to other business—leaving the patient to lie for an hour with wires trailing from her vulva to a box of electronics. Resulting psychological effects can disturb the measurement.

Finally, in a relatively small number of patients, the tube or rod used to advance the forward sensor into the bladder may irritate the opening of the urethra into the bladder, and this irritation may cause spurious indications from the instrumentation. In particular, such irritation may have a slight tendency to produce an emulation of bladder instability, or to suppress an already existing tendency toward bladder instability. On the other hand, such irritation may also have some very slight tendency to stimulate the urethral sphincter to close either more or less forcefully than it customarily does—thereby either suppressing or emulating the observable characteristics associated with genuine stress incontinence.

Although this last-mentioned set of problems is not a major drawback, it is of some interest in relation to my invention, as will be seen.

(e) Diagnostics: Externally Stabilized Catheter—Doctors Sutherst and Brown of the University of Liverpool have described their studies of incontinence diagnosis making use of a two-channel catheter with a proximal end of one channel positioned within the urethra. 34 *Urologia Internationalis* 403 (1979), 52 *British Journal of Urology* 138 (1980), 53 *British Journal of Urology* 360 (1981).

In some of these studies the catheter was stabilized to the exterior of the patient's body to "prevent movement due to its weight and connections". The stabilization was accomplished by means of a "spring paper clip fixed to a flexible ring pessary . . . held between the patient's thighs".

Although these studies offered favorably high correlations between observed liquid discharge and other indications of "genuine stress incontinence," the experimental arrangements were in several ways marginal from the viewpoint of an individual clinician. The external appliance worn by the patient to stabilize the catheter would produce considerable patient discomfort if the patient were to bend, stretch, or even walk, since the urethral meatus in particular (which would be abraded by such activities) is very sensitive. Consequently in the studies described the patient could only be "tilted to the erect position on a motorised bed." Such an apparatus, of course, is far beyond the scope of equippage for the vast majority of individual clinicians.

In addition, the appliance would tend to fix the rearward end of the tube too securely to the patient's body, preventing effective incorporation of the "Q-tip test" into the diagnostic apparatus and method. As will be apparent, all of these limitations would very severely limit the feasibility of the published method for practical everyday clinical use.

(f) Diagnostics and Antiincontinence Prosthetic Therapy: the Intravaginal Pessary—I turn now from prior-art diagnostics to prior-art efforts to actually relieve the symptoms of incontinence. It will be seen, however, that some therapeutic devices have been used in a diagnostic mode.

As previously mentioned, the bladder and the urethra are subjected to various intraabdominal pressures in common in the normal woman, but selectively in the incontinent woman due to urethral prolapse. Furthermore sphincter action as such is weakened.

As also mentioned above, corrective surgery elevates the vagina and the urethra above the levator ani sling to equalize intraabdominal pressure on the urethra and bladder, thereby making the most of whatever muscular action remains. Although surgery has several serious limitations, efforts to substitute milder therapy such as prosthetic aids to erecting the urethra have heretofore been quite unsatisfactory.

One type of device, known as a "pessary," is inserted into the vagina with the object of longitudinally stretching the vagina—and with it the adjacent urethra. Thus such devices parallel in rational the surgical strategy. There are some three or four different kinds of pessaries, all with their own problems.

Generally they are all unsatisfactory in that they are very traumatic to the vaginal epithelium, causing ulceration and infection.

The various kinds are also all unsatisfactory in that the patient has been unable to insert them; they have required insertion by a physician. This is a very important drawback since it leads almost inevitably to inadequately frequent cleaning, and consequently to unsanitary conditions, infection, and aggravated ulceration.

For these reasons the prior-art pessaries considered as a group have not been very popular. Some discussion of individual kinds of pessaries, however, is in order.

Some pessaries are made of soft rubber or plastic formed on a wire skeleton. These were first introduced for the purpose of supporting a patient's uterus after prolapse. (This latter condition is a falling of the uterus into the position of the vagina, due to age or history of multiple childbirths.) It was then incidentally found that these pessaries prevented incontinence in some women. Such covered-wire pessaries generally have taken the form of a long letter "O" bent at a right angle near its top end, to form a tall vertical letter "U" that is joined at the open end to a short horizontal letter "U". Viewed from the side, the shape is thus that of an inverted letter "L".

To install this device, a physician squeezes the opposing sides of the frame together and inserts the pessary, with its short horizontal portion leading, into the patient's vagina. In principle the shorter U-shaped section fits around the patient's cervix, and ideally the physician should not let the opposing sides of the skeleton spring apart until the pessary is entirely into position.

In practice, of course, it is virtually impossible for the physician to hold the opposing sides apart after the pessary is about two-thirds inserted, so the device must be inserted the rest of the way while sprung open. It will be appreciated that there is some patient discomfort in this process, and possible trauma as well. Moreover, since the bottom or distal end of the device is a solid transverse bar across the mouth of the vagina, it is exceedingly difficult for the physician to verify the correct positioning of the upper structure of the pessary relative to the cervix, at least without further discomfiting the patient.

Following the discovery that these devices offered some relief to certain incontinent women, and following sophisticated research to determine the mechanism by which this relief was obtained, there have been attempts to produce articles more suited to routine intravaginal use for control of incontinence. One relatively promising line of approach has involved molded pessaries. These were made of heat-softenable materials so that they could be immersed in warm water and then narrowed, lengthened, widened or shortened by manual kneading to more nearly match the shape of the vaginal canal.

All these attempts have met with little success. Prior-art pessaries have been problematic either in terms of discomfort, pressure necrosis and ulceration, if they have been made adequately tight-fitting; or in terms of expulsion with any sudden increase of intraabdominal pressure, such as coughing, if they are not tight enough.

Such disadvantages are virtually predictable from the overall demands placed upon prior-art pessaries: they are inherently subject to opposing constraints or expectations that have not been satisfactorily resolved. In particular, such pessaries are required to laterally engage the vagina by friction to hold themselves in place, but nevertheless to be slidable all the way up into the vagina for maximal elevating effect. Furthermore such pessaries are expected to conform to the internal shape of the vagina, for a reasonable degree of patient comfort; but also nevertheless to be readily removed and replaced, for a reasonable degree of sanitation. None of the prior-art pessaries has been conceptualized with an adequate eye to these intrinsic conflicting requirements.

Some patients have used tampons to elevate the vagina, but in protracted use these have caused problems because of their highly absorbent materials, leading to excessive dryness and consequent irritation of the vagina. To avoid these problems a foam-rubber substitute has been introduced. Its efficacy is not yet reported, but it does not extend fully into the most proximal portion of the vagina, behind the cervix, and therefore does not achieve optimal elevation of the vagina and urethra. Moreover, by the reasoning outlined in the preceding paragraph such a device is inherently likely to be either inadequate in elevating the vagina and urethra, and possibly difficult to keep in place, or traumatic to the vagina and difficult to keep clean.

Although pessaries thus have been relatively problematic as therapeutic prosthetics, their use in diagnosis has been proposed. Doctors Bergman and Bhatia, for example, have reported evaluation of the "pessary test" as a clinical tool to predict successful outcome of impending antiincontinence surgery. XXIV *Urology* 109 (July 1984).

In this research it was observed that the patterns of intraabdominal, intravesical, and intraurethral pressure observed with a pessary emulated to a certain degrees the corresponding patterns observed after surgery. This report is limited, however, to a statement that the pressures observed after surgery "were found to be very similar" to the corresponding pressures observed with a pessary emplaced before surgery. No patient-by-patient comparisons, no numerical abstractions, no control tests (i.e., patients with bladder instability or other nonanatomical syndrome), and no actual clinical effort to screen patients based upon a "pessary test" were reported.

(g) Antiincontinence Prosthetic Therapy: the Bonnar Inflatable Urethral Dam—A more direct approach to controlling incontinence is to obstruct the urethra. One device that aims to accomplish this is known as the "Bonnar device"—a partially inflatable article of soft silicone rubber. This device consists of an inflatable generally spherical main body and noninflatable rabbit-ear-shaped protrusions that fit into the lateral fornices of the vagina. (These are the most proximal region of the vagina, adjacent the cervix.)

The device is stabilized within the patient's vagina by the fornical protrusions, while the primary spherical section of the device when inflated presses forcibly against the wall between the vagina and the urethra. This inflated spherical section actually operates as a prosthetic sphincter, squeezing the urethral channel against the bone structure posterior to the urethra and thus directly blocking the urethra.

Unfortunately, unlike the natural urethral sphincter, this prosthesis is not remote controlled; consequently the Bonnar device must be deflated when the patient wishes to void. It must also be reinflated afterward. Although the device need not be extracted for this purpose, even the necessity of deflating and reinflating it is particularly objectionable since these steps severely encumber the patient's ability to approximate normal toilet behavior. For most patients this requirement would constitute an extremely undesirable limitation on the regular pursuit of ordinary daily activities.

It has been reported in one test of twenty research subjects that commercial versions of the Bonnar device were too large or too small for eight individuals, were totally ineffective in more than ten individuals, and were rejected for personal use after the trial by eighteen.

The Bonnar device is of interest here only because part of it is inflated within the vagina, and because it is intended to alleviate incontinence. Although it has been misdescribed in some literature as producing "elevation" of the urethra, this device actually does no such thing, but rather operates by direct occlusion in lieu of the normal sphincter, as already stated.

(h) Other Related Devices—Two other clinical articles should be mentioned briefly because they are inflatable and are inserted into the vagina, though their purposes and functions are quite different from those of the present invention.

One of these devices is known as the balloon of Kegel. It is placed in the vagina and connected to a manometer or other pressure meter, to measure the pressure with which a post-childbirth patient is able to "squeeze" inwardly with the vagina. This monitoring was initially introduced as part of a program (familiarly known as "Kegel's exercises") to determine postpara improvement in muscle tone. The balloon is inflated for the measurements, kept attached to the manometer during the monitoring, and immediately afterward deflated and removed from the patient. To make these measurements there is no particular need to advance the balloon fully into any well-defined position within the vagina. Only a physician normally performs the insertion, inflation, deflation, and removal.

Another device, which like Kegel's balloon has fallen rather out of popularity, is a balloon with attached button-like electrical contacts in its exterior surface. This article is part of a system used for artificially stimulating and thus exercising the muscles of the pelvic floor. The balloon is quite short, and many patients find the electrical button contacts—even when not energized—quite uncomfortable.

3. OTHER NEW TECHNIQUES: THE INTERNALLY STABILIZED CATHETER

My previously mentioned copending patent application describes a catheter that is internally stabilized within the patient's urethra during diagnostic examination, providing a conduit for direct discharge of any fluid from within the urethra to the outside of the patient's body.

That catheter device is amenable to normal movement of the patient during examination, and provides a much more positive exhibition of discharge characteristics. It usually supplies enough information for dispositive diagnostic distinction between anatomical incontinence and bladder instability. It is also compatible with the "Q-tip test."

It will be understood that the catheter device mentioned here is not prior art with respect to the present invention. In addition, the present invention does not directly improve upon my earlier device, but rather takes an entirely different approach to diagnosis.

My earlier catheter device, however, is somewhat less quickly used, and does require somewhat greater sophistication on the part of the diagnostician, than the present invention. Furthermore, and most important, the earlier catheter device does not itself relieve symptoms of anatomical or "genuine stress" incontinence; it is limited to pointing the way for the type of treatment that would be suitable.

My earlier catheter device remains highly useful to confirm the findings of the present invention, when such confirmation is desired. It may be particularly useful in certain cases in which results of diagnosis with the present invention are inconclusive; such results may arise, for instance, when a patient has both anatomical incontinence and bladder instability.

BRIEF SUMMARY OF THE INVENTION

My invention is a device for relieving or diagnosing incontinence in a woman. This device includes an elongate body that is very generally shaped and sized for insertion into the patient's vagina.

The invention also includes some means for adjustably inflating the elongate body and for sealing it. These "inflating and sealing means" are permanently attached to the elongate body, and maintain the inflation over at least many hours.

Due to this inflation the elongate body laterally engages the vagina to retain the elongate body in the vagina, and longitudinally distends the vagina and with it the patient's urethra. These conditions are maintained over protracted periods.

The elongate body has near its proximal end an indentation to receive the woman's cervix—while the elongate body extends into and distends the most proximal portion of the vagina posterior to the cervix. The elongate body has this indentation at least when inflated within the vagina, but the indentation may become imperceptible or may even be absent when the body is deflated, or when it is inflated elsewhere.

The inflating and sealing means are sufficiently compact and otherwise suited for the woman to carry, in or near her vagina and attached to the elongate body, while she pursues normal daily activities.

By virtue of these characteristics of my invention, the urethra is elongated, and the woman's bladder neck and the proximal portion of her urethra are moved toward normal intraabdominal positions, when the device is inflated within the vagina.

In addition, in preferred embodiments of my invention the elongate body also has near its base at least a slight lateral enlargement which fits just above such woman's levator ani sling to help retain the elongate body within the vagina. This enlargement preferably encircles the elongate body. As will be recalled, the levator ani sling surrounds the base of the vagina, and is often so badly weakened in the anatomically incontinent woman that it aggravates the prolapse of the urethra and its sphincter by allowing them to essentially embed themselves in the levator ani sling. Thus the lateral enlargement near the base of the elongate body tends to compensate for the weakness of the levator ani sling—forcing the latter to serve as a pedestal for support of the elongate body and consequently of the longitudinally distended vagina.

Like the indentation mentioned earlier, this enlargement is present at least when the elongate body is inflated within the vagina, though it may be imperceptible or absent when the elongate body is not inflated within the vagina.

It is also preferable that the lateral enlargement be inflatable to engage the levator ani sling, so as to facilitate retention of the elongate body within the vagina. The lateral enlargement and the elongate body together preferably form a substantially unitary inflatable chamber that is suited for inflation "all at once" through the inflating and sealing means.

Preferably the inflation means include a flexible airtight chamber within the elongate body, and a valve and fitting in the body—that is, in the wall of the body—for use in inflating or deflating the chamber. The valve should be manually operable from the distal end of the elongate body while the elongate body is within the vagina. The fitting is accessible at the distal end of the elongate body for attachment of a source of compressed gas, while the elongate body is within the vagina.

My invention also preferably includes some means for stiffening the elongate body while it is deflated, to facilitate insertion into the vagina. These "stiffening means" advantageously include a longitudinal cavity that is formed within the elongate body. The longitudinal cavity is open at the distal end of the elongate body, extending through the body to a point near the proximal end of the elongate body. The cavity is adapted to receive one of the patient's fingers to push the elongate body into the vagina. It is possible to use a rod or other appliance instead of a finger, although doing so sacrifices the advantage of tactile guidance in positioning the elongate body at the proximal end of the vagina.

The exterior of the elongate body, unlike many or all of the prior-art pessaries, is particularly adapted for nontraumatic contact with the interior of the vagina. Thus, for example, unlike the elastomer-covered-wire pessaries it is not made to press outwardly with spring-metal force upon the walls of the vagina. Unlike the manometer used with Kegel's balloon, the "inflating and sealing means" of my invention are suitable for maintaining the inflation of the elongate body during at least many hours without any external pneumatic attachment. Unlike the electrical-stimulation apparatus mentioned earlier, my device is without electrical components or connections.

My invention is preferably shaped and sized in such a way, and is preferably inflated enough, that it produces a degree of elongation of the urethra, and a degree of movement of the bladder neck and proximal portion of the urethra toward normal intraabdominal positions, which are sufficient to render the urethra capable of withstanding bladder pressures characteristic of anatomical incontinence. Thus the device when inflated within the vagina relieves symptoms of anatomical incontinence.

On the other hand, the device preferably is shaped and sized in such a way, and is inflated gently enough, that the elongation of the urethra, and the movement of the bladder neck and proximal portion of the urethra toward normal intraabdominal positions, are generally insufficient to render the urethra capable of withstanding bladder pressures characteristic of bladder instability. Thus the device facilitates diagnostic distinction between anatomical incontinence and bladder instability.

The elongate body of my invention is adapted for insertion by the patient herself and is wholly flexible.

My invention also provides a method for relieving or diagnosing incontinence in a woman. This method includes the steps of:

(1) inserting into the woman's vagina an inflatable elongate body that is very generally shaped and sized to fit within the vagina, and that has, at least when inflated within the vagina, an indentation near the proximal end of the elongate body to receive the woman's cervix while the elongate body extends into and distends the most proximal portion of the vagina posterior to the cervix;

(2) then adjustably inflating the elongate body, so that the elongate body (a) laterally engages the vagina to retain the elongate body within the vagina, (b) longitudinally distends the vagina and with it the woman's urethra, and (c) moves the woman's bladder neck and proximal portion of her urethra toward normal intraabdominal positions;

(3) sealing the elongate body to maintain the inflation—and thereby to maintain these three beneficial functions just enumerated—over at least many hours; and (4) then leaving the elongate body so inflated within the vagina over at least many hours—which, to repeat once again, continues the three functions stated above.

In this method the elongate body preferably has the various features described above for the device of my invention.

In particular the device preferably has a slight lateral enlargement at the distal end, and the inflating step preferably includes inflation of the lateral enlargement to engage the levator ani sling, thereby facilitating retention of the elongate body within the vagina.

The inflating step preferably includes affixing a source of compressed gas to the valve and the fitting, while the elongate body is within the vagina, and supplying such gas from the source through the valve and fitting into the elongate body.

The method also preferably includes the step of (before or during the insertion step, or both) stiffening the elongate body while it is at least mostly deflated, to facilitate the insertion step. To expedite the stiffening step, a longitudinal cavity is preferably formed within the elongate body, as previously described, adapted to receive one of the patient's fingers. The stiffening step accordingly includes inserting fingers into the cavity to push the elongate body into the vagina.

Preferably all of these recited steps can be (and are) performed by the patient herself.

When it is practiced for diagnosis of the woman's previously reported symptoms of incontinence, the method preferably includes two final steps (after at least a protracted part of the "leaving" step). The first of these final steps is determining whether the previously reported symptoms of incontinence were relieved.

The second is the step of diagnosis itself. Specifically, this last step is diagnosing the patient's incontinence as arising from anatomical incontinence if the previously reported symptoms were relieved; and diagnosing the woman's incontinence as arising from bladder instability if the previous symptoms were not relieved.

The preceding discussion shows that my invention, and my invention alone, satisfactorily resolves the conflicting constraints upon devices to be worn within the vagina for elevation of the urethra. This invention alone is (1) capable of conforming closely to the internal contours of the vagina—providing both effective frictional engagement to avoid expulsion and at the same time maximal patient comfort—and nevertheless (2) capable of being easily emplaced by the patient herself without discomfort, and being readily removed by the patient herself for cleaning as frequently as may be desired.

Because my invention is not called upon to make compromises as to efficacy of elevation or stability of emplacement, it is totally effective in almost all patients suffering from anatomical incontinence. Yet even while inflated in place my invention does not prevent voiding.

As to diagnostic use, my invention is greatly improved relative to all prior art. It is quickly and easily emplaced, inflated, and removed, whether by the examining physician or an attendant or the patient herself, without patient discomfort. Because of its extremely consistent effectiveness in eliminating the symptoms of anatomical—but not neurological—incontinence, it also provides an extremely reliable diagnosis.

All of the foregoing operational principles and advantages of the present invention will be more fully appreciated upon consideration of the following detailed description, with reference to the appended drawings, of which:

BRIEF DESCRIPTION OF THE DRAWINGS

In FIG. 2, however, the inflation bulb has been omitted.

FIG. 10 is a sectional elevation, similar to FIG. 4, of the FIG. 9 embodiment. In this drawing the shape of the longitudinal cavity has been distorted for clarity, as will be explained in the text that follows.

DETAILED DESCRIPTION OF PREFERRED EMBODIMENTS

Figure 1:
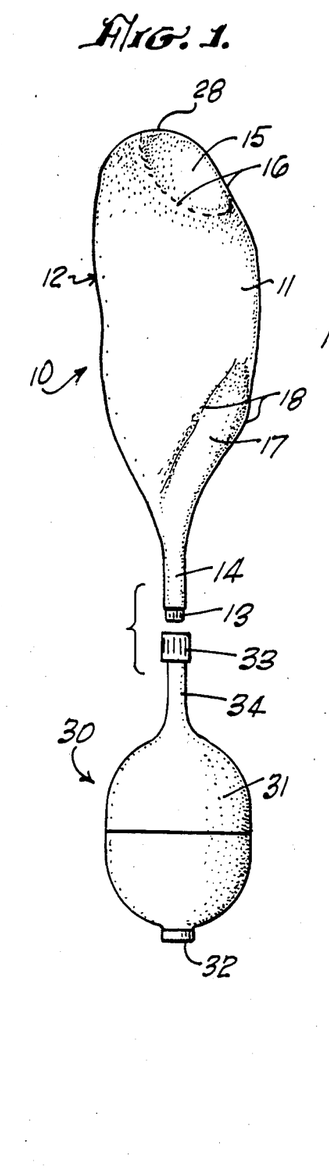
FIG. 1 is a first elevation showing one preferred embodiment of the device of my invention, with inflation bulb attached. The shapes illustrated in this drawing and the others, except as otherwise specified below, are the shapes assumed by the various embodiments when respectively inflated within a patient's vagina. Further, the drawings are not to scale.
Figures 2, 3:
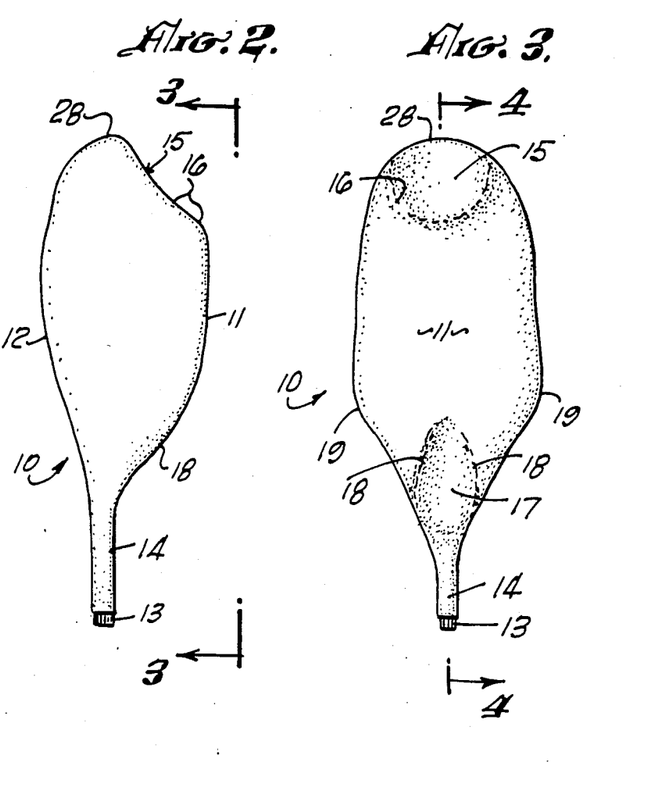
FIG. 2 is a second elevation, taken at a horizontal angle of about forty-five degrees to the first, of the FIG. 1 embodiment.
FIG. 3 is a third elevation, taken at right angles to the second (which is to say, along line 3—3 of FIG. 2), of the FIG. 1 embodiment.

As shown in FIGS. 1 through 3, one preferred embodiment of my invention includes an elongate body 10, with an attached inflation fitting 13. The elongate body 10 is made of any suitably pliable but strong elastomer, with external surface selected for relatively long-term compatibility with vaginal tissues. The elastomeric body should be compliant, so that it can repeatedly expand when inflated and shrink when deflated. The inflation fitting is made to attach to a mating fitting 33 of a conventional inflation bulb 30, and to seal the elongate body when the mating fitting 33 is not attached.

The portions of the elongate body 10 and of the inflation bulb 30 that respectively carry the inflation fitting 13 and the mating fitting 33 are preferably formed as relatively narrow tubes 14 and 34. This configuration permits attachment of the mating fitting 33 to the fitting 13 of the elongate body 10 while the latter is within a patient's vagina, but while the relatively bulky portions of the inflation bulb are spaced away from the patient's labia sufficiently for comfort and convenience during inflation of the elongate body.

The inflation bulb has a controllable one-way valve 32. During inflation this valve 32 admits air to the bulb 31 but prevents escape of air from the bulb 31. The user can release the valve 32, however, to permit escape of air from the bulb 31 and the elongate body 10, to deflate the device 10 when desired. If preferred, a controllable valve may be used in the fitting 13 on the elongate body 10 itself, to facilitate deflation.

The illustrated shape of the elongate body 10 FIGS. 1 through 3 is that shape which the elongate body assumes when it is inflated within the patient's vagina.

The shape illustrated is determined from an actual mold that was taken from the vagina of a normal woman. The mold shows clearly that the posterior vaginal wall is almost a third again longer than the anterior vaginal wall. Suitable use of this information gives the device a much better fit: in particular, the posterior wall 12 of the elongate body 10 is correspondingly longer than the anterior wall 11 of the body 10.

Figures 4, 5:
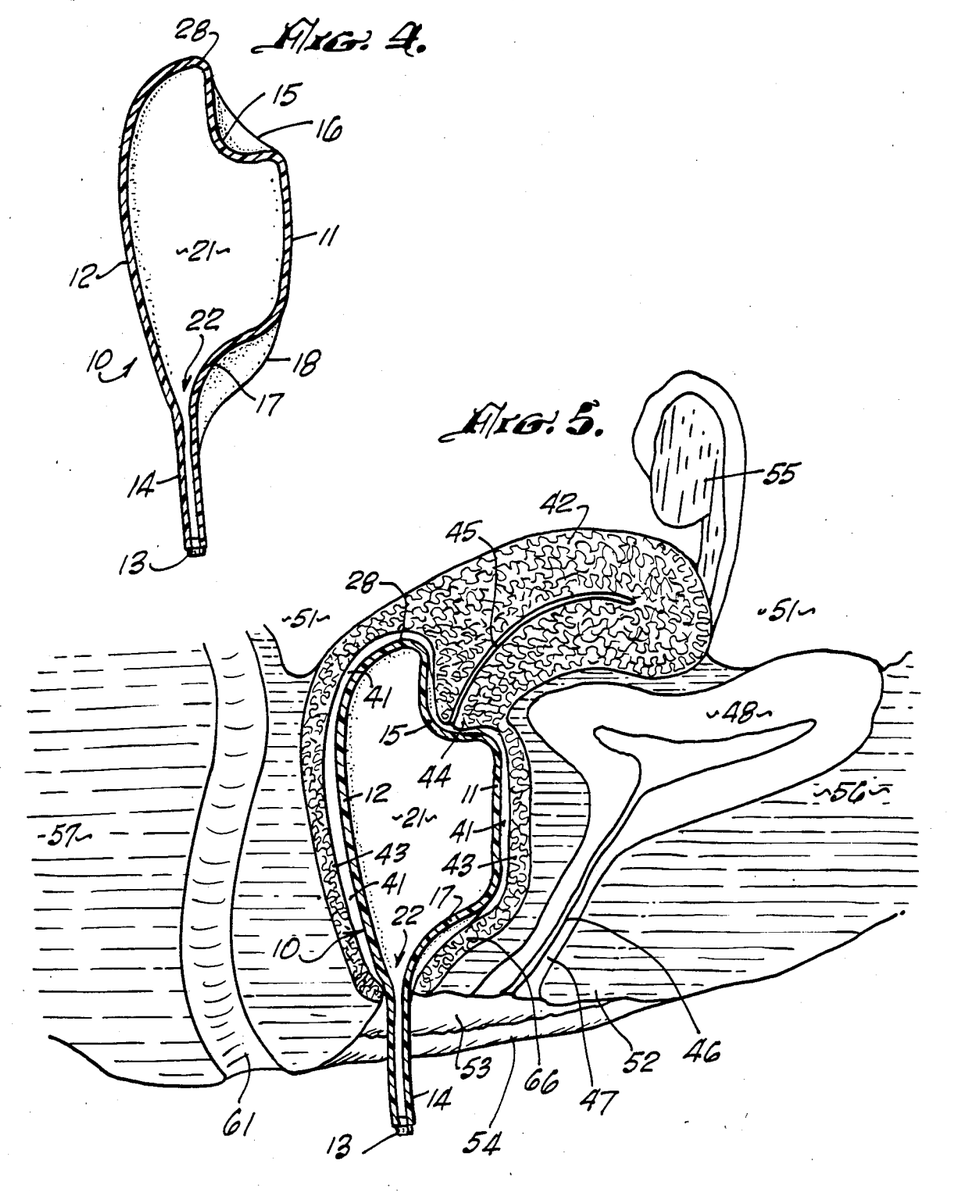
FIG. 4 is a sectional elevation taken through the central plane of the FIG. 1 embodiment and at the same angle as FIG. 2 (which is to say, taken along the line 4—4 in FIG. 3), and showing the inflatable inner chamber.
FIG. 5 is a cross-sectional elevation at the same plane as FIG. 4, but also showing in a very schematic fashion the bladder, urethra, vagina, and related parts of a woman's abdomen, with the FIG. 1 embodiment shown inserted into the vagina and inflated to longitudinally distend the vagina and urethra.

Further, and as better understood with the aid of the cross-sectional view in FIG. 4, the elongate body 10 is a hollow shaped shell, whose walls 11, 12, 28, 14, 15, 17 define an inflatable chamber 21 and an inflation conduit 22. FIG. 4 also shows that a generally cup-shaped or rounded concavity or indentation 15, defined by a peripheral ridge 16, appears near the proximal (with respect to the vagina) end of the elongate body 10. This indentation 15 is offset relative to the tip 28 of the elongate body 10. Another indentation 17, less pronounced but elongated in the same direction as the elongate body 10 generally, is defined by angled ridges 18 near the distal end of the elongate body, in the region where the elongate body is tapering toward the inflation tube 14.

FIG. 5 illustrates the use of the device 10 and the purposes of the two indentations 15 and 17. This drawing represents the vaginal epithelium or skin 41, the uterus 42 and the extensions 43 of uterine tissue into the region surrounding the vaginal epithelium 41, the cervix 44 terminating the uterine canal 45, and the urethra 46 with its surrounding tissue 47, leading from the bladder 48. Also shown for purposes of orientation only are the body cavity 51, clitoris 52, labium minus 53, labium majus 54, ovary 55, anterior abdominal wall 56, buttocks 57, and anus 61. Thus the anterior portion or front of the patient's body is toward the right-hand side of the drawing, and the posterior portion or back is toward the left-hand side.

From FIG. 5 it may be seen that the cup-shaped concavity 15 is provided to receive the patient's cervix, while the tip 28 itself of the elongate body 10 extends into and distends the most proximal portion of the vagina posterior to the cervix.

Not shown explicitly in this drawing is the levator ani sling, which as previously mentioned is a hammock-shaped musculature extending across the bottom of the body cavity. The levator ani sling passes just above the mouths of the urethra 46 and vagina 41, 43, and in particular it encircles the vagina in the region 66 where the anterior vaginal wall is shown angled at about forty-five degrees to the vertical. The broad trench-shaped concavity 17 in the elongate body 10 thus accommodates the levator ani sling. In particular the concavity 17 accommodates that musculature when the patient is "squeezing" the levator to forcibly close the mouth of the vagina, or—in a normal patient—when the patient is not actively squeezing but the levator has sufficient tone remaining to constrict the mouth of the vagina somewhat.

These accommodations of the internal features of the patient's body constitute an improved fit, which helps avoid ulceration and infection as well as discomfort.

As previously mentioned, however, the illustrated shape of the elongate body 10 in FIGS. 1 through 3 is that shape which the elongate body assumes when it is inflated within the patient's vagina. In various embodiments of my invention—depending upon the age and other condition of the patient, the intended method of installation, and other factors—the several illustrated features 15, 16, 17, 18 may be imperceptible or even absent when the elongate body 10 is not inflated, or is inflated elsewhere.

Thus, for example, if the device 10 is to be emplaced simply by pushing it into the vagina from outside the labial region 53, 54, without any other guide conduit or the like, then for many patients the device 10 must be relatively stiff so that it maintains a relatively elongated shape even when uninflated or only very slightly inflated. In such cases the wall 11, 12, 14, 15, 17, 28 of the elongate body must be relatively thick, and therefore preferably should be molded with the various illustrated features 15, 16, 17, 18 permanently defined. Otherwise uncomfortable or traumatic forces may be exerted against the inside of the vagina in regions where the wall of the elongate body must bend abruptly—near the cervix 44 or just above the region 66 adjacent the levator ani sling.

On the other hand, some physicians or some patients may prefer to emplace the device 10 in a manner similar to that often used in emplacing a tampon: a cardboard or like stiff cylinder is inserted fully into the vagina, into the region just posterior to the cervix 44, and a slender rod is inserted into the cylinder to hold the device 10 in position while the cylinder is withdrawn from the vagina. This type of insertion may have clinical advantages, again depending upon the age and other condition of the patient, and other factors. In this case the wall 11, 12, 14, 15, 17, 28 of the elongate body 10 need not be as thick; in fact, to facilitate insertion of the elongate body 10 into a cardboard cylinder of suitable diameter, a smaller wall thickness will be preferred. In a device of this type the features 15, 16, 17 and 18 need not be as plainly defined, and may even be absent when the device 10 is uninflated or is inflated outside the vagina.

It will be appreciated that innumerable variations of wall thickness and extent of definition of the features 15, 16, 17, 18 will be found most suitable for the innumerable clinical circumstances and the innumerable preferences of physicians and patients, all encompassed within the scope of my invention.

I contemplate, however, that for most embodiments of my invention a single size will probably fit almost any woman comfortably but firmly, by virtue of the inflation that is an inherent part of the device 10.

When the vagina is distended, and particularly when the posterior portion of the vagina behind the cervix is distended to elevate or erect the vagina, the anterior vaginal wall stretches and thus elevates or erects the functional part of the urethra 46, 47. The distension also moves the bladder neck and the proximal one-third of the urethra up into their normal intraabdominal positions, so that abrupt increases in pressure are applied to the proximal urethra from the surrounding tissues, as well as to the bladder, thus equalizing ejection pressure and damming pressure as in the normal woman.

The effect, however, is usually not sufficient to prevent urinary ejection by abrupt increases that are neurologically amplified as in "bladder instability." Consequently the efficacy of the device for a particular patient is itself indicative of the type of incontinence present in that patient.

The incontinence device may be used for diagnostic procedures as follows. If an incontinence diagnostic device such as described in my previously mentioned copending patent application is available and has been used to demonstrate anatomical incontinence, then the present device 10 is inserted and insufflated and stressful maneuvers are repeated. If the patient is continent in these maneuvers, this is confirmatory evidence that she has true anatomical incontinence and is a candidate for an operative procedure for correction—or for temporary prosthetic therapy by use of the present device 10 itself, or both.

If, however, the patient's incontinence persists with the device inflated, then this is contrary evidence that she has bladder instability and is a candidate for treatment by medication.

Yet again, if a diagnostic device such as described in my copending application is not available, then the present device 10 may be used in the manner described above to obtain a first diagnosis; if this diagnosis proves marginal or ambiguous, as may happen in a very small number of cases, other methods may be used for elucidation of the patient's condition.

It will be noted from FIG. 5 that my new device 10 when properly inflated presses only lightly against the region of the urethra—by virtue of the size and particularly of the broad-fronted shape of the anterior walls 11, 17, 18 of the device 10. This limitation of pressure against the urethra preserves the patient's ability to void, circumventing the principal drawback of the Bonnar device. The pressure limitation also prevents patient discomfort, as well as pressure necrosis and ulcertion of the vaginal mucosa. Thus the invention has none of the clinical problems of previous antiincontinence pessaries.

Similarly, since the new device is inflated and therefore inherently takes the shape of the vaginal canal, it eliminates time-consuming manual procedures by skilled personnel, such as required with the prior-art moldable pessaries mentioned earlier.

In some patients, degradation of the levator ani sling has advanced to such a degree that unsatisfactorily high inflation pressures may be required to retain my device 10 in the vagina. In such instances continence generally will be achieved through use of another preferred embodiment of my invention, illustrated in FIGS. 6 and 7.

In this embodiment the elongate body 110 has generally the same features as that of the previously discussed embodiment: an inflation fitting 113 and tube 114, a concavity 115 defined by a circumferential ridge 116 near but anterior to the tip 128, and possibly a less-pronounced trough-shaped concavity 117 defined by ridges 118 near the bottom of the elongate body 110. (The reference numerals used in FIGS. 6 and 7 parallel those used in the earlier drawings, but with a prefix "1" applied to each to distinguish the features of this embodiment.)

Figure 6:
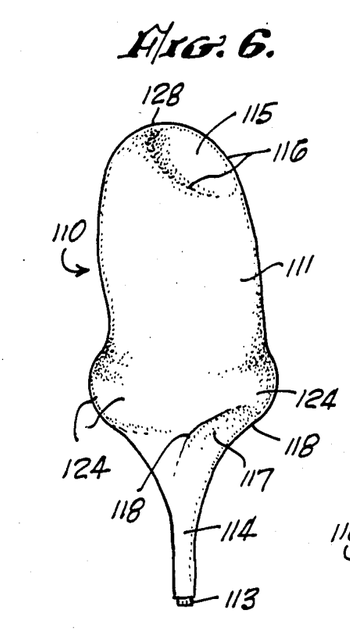
FIG. 6 is an elevation similar to FIG. 1, but showing another preferred embodiment that has a ring-shaped lateral enlargement near its base.
Figures 7, 8:
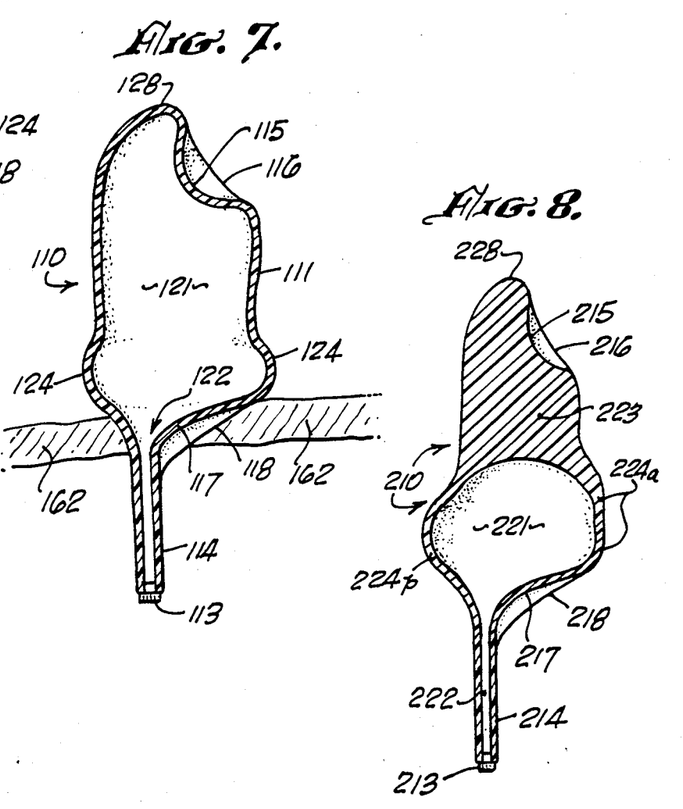
FIG. 7 is a sectional elevation similar to FIG. 4, of the FIG. 6 embodiment, but also showing generally the levator ani sling, and showing generally the relationship between the ring-shaped lateral enlargement and the levator ani sling when the device is in place.
FIG. 8 is a sectional elevation, similar to FIG. 7, of a variant of the FIG. 6 embodiment.

The embodiment of FIGS. 6 and 7, however, also has a peripheral enlargement 124 that encircles the elongate body 110 near the bottom or distal end, just above the levator ani sling—which is shown very schematically at 162 in FIG. 7. The enlargement 124 thus forms with the levator ani sling 162 a pedestal upon which the vagina and urethra are erected. The enlargement 124 may be formed in the lower wall of the elongate body, defining part of a unitary inflatable chamber, as illustrated in FIG. 7.

If preferred for clinical or other reasons the enlargement 124 may be formed as a separate chamber (not illustrated) that is separately inflated. In the latter case the separate chamber may occupy essentially the entire cross-section of the lower part of the elongate body, with only an inflation conduit passing from an inflation fitting outside the vagina to the upper part of the elongate body; or alternatively the separate chamber may be formed as an inflatable annulus whose inside diameter is roughly the same as the outside diameter of the inner chamber. It will be appreciated, once again, that a number of variants are possible within the scope of my invention.

With respect to all such variants I consider it highly preferable to avoid structures and inflation-pressure requirements that could cut off conduction through the urethra, thus forcing the patient to deflate the device in order to void. Hence the enlargement 124, or at least that portion of it which is anterior to the main bulk of the elongate body 110, should not be so pronounced or so strongly inflated as to block the urethra. The broadly inflated anterior wall 111 of the elongate body 110 helps somewhat in distributing the inflation pressure to minimize this consideration, but it must be kept in mind in designing (and in inflating) the enlargement 124.

One class of variants of the lateral-enlargement embodiment of my invention that is particularly noteworthy appears in FIG. 8. Although I prefer the FIG. 7 embodiment to this variant, I believe that the FIG. 8 variant is usable. (In FIG. 7 the features common to earlier drawings have the same reference numerals but with the prefix "2.")

Here the upper section of the elongate body is filled with material, as at 223, rather than being inflatable as in the configurations discussed earlier. Only the lower section is made to form an inflatable chamber 221.

In the FIG. 8 variant, at least the outer portions of the solid section 223 should be somewhat resilient. In addition, the upper section 223 should be more slender than the inflated contour illustrated in the earlier drawings, since it must be inserted without benefit of deflation to minimize patient discomfort and trauma. Particularly in this variant it will likely be important to ensure that the anterior face 224a of the lateral enlargement is broadened—at least when inflated within the vagina—so that there is minimal localization of pressure against the urethra. The lateral enlargement may, however, be fully defined at its posterior face 224p and at the sides (extending out of the plane of the paper).

Figure 9:
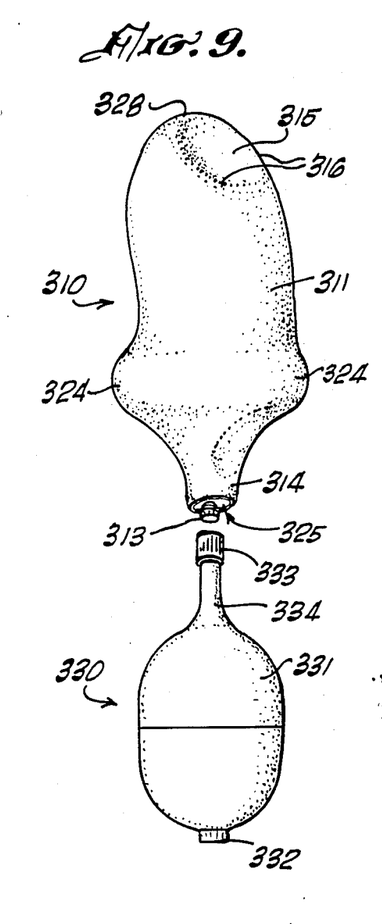
FIG. 9 is an elevation similar to FIG. 1, but showing yet another preferred embodiment that has a longitudinal cavity, open at the bottom, to facilitate manual stiffening of the device for insertion.
Figure 10:
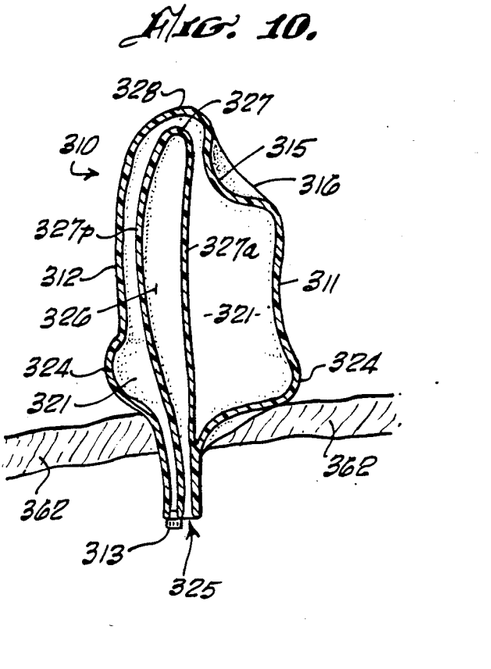

FIGS. 9 and 10 illustrate another preferred embodiment of my invention, one which is particularly configured for easy insertion into the patient's vagina. This embodiment has an inner cavity 326, with an opening 325 to the outside of the device. The opening 325 is at the bottom or distal end of the elongate body 310, so that it is accessible from outside the patient's body. The inner cavity 326 is defined by a very generally cylindrical internal wall that includes an anterior face 327a and a posterior face 327p, as well as lateral faces (not shown) that extend out of the plane of the paper.

(It is to be understood that when the device is inflated the opposing walls 327a, 327p, etc., of the longitudinal cavity 326 tend to be pushed together. In FIG. 10, however, the cavity is shown opened. This departure from realism is simply for the purpose of clarity in illustrating the inner cavity. In FIGS. 9 and 10 the features common to earlier illustrations have the same reference numerals, but with the prefix "3.")

Thus the internal wall 327a, 327p, etc., cooperates with the external wall 311, 312, etc. to make the inflatable chamber 321 annular, at least in the lower sections of the elongate body 310. As illustrated in FIG. 10, the internal wall may be made with its own tip section 327 so that in the tip region the inflatable chamber 321 is not annular.

If preferred, however, the internal wall may be connected at the top to the inside surface of the outer-wall tip 328, so that the inflatable chamber 321 is annular all the way to the top. This configuration is not illustrated. As will be appreciated, such an embodiment may be somewhat easier to use in that the contours of the cervix are more readily felt through a single layer of material; whereas the illustrated embodiment is somewhat stronger and perhaps more readily constructed.

Although FIGS. 9 and 10 illustrate a lateral enlargement 324 such as that discussed in relation to FIGS. 6 through 8, it is to be understood that in another embodiment of my invention the internal-cavity feature which is illustrated in FIGS. 9 and 10 may be provided while the lateral enlargement 324 is omitted. Such an embodiment would likely be useful, in particular, for women in whom degradation of the levator ani sling is not very advanced To use the embodiment of FIGS. 9 and 10, the patient first applies a suitable lubricant such as petroleum jelly to the inside of the internal wall 327, 327a, 327p, etc. In doing this the patient is careful to avoid applying any of the lubricant to the outside of the external walls 311, 312, 315, etc.

The patient then inserts one of her fingers into the internal cavity 326, with the valve 313 facing away from her (i.e., toward the back side of her hand) and with the upper concavity 315 facing toward her (i.e., toward the palm side of her hand).

Figure 11:
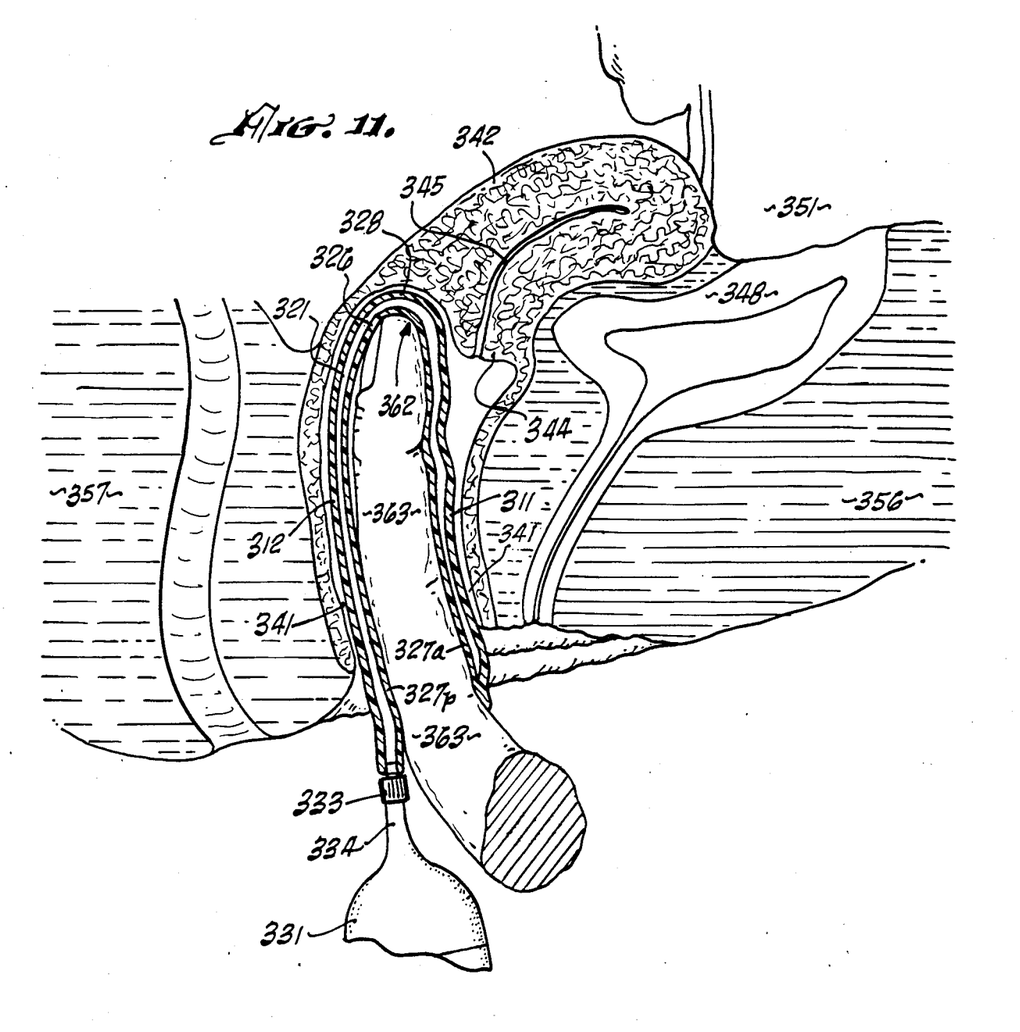
FIG. 11 is a sectional elevation similar to FIG. 5, but illustrating part of a procedure for emplacing the embodiment of FIGS. 9 and 10.

As shown in FIG. 11, the patient then inserts her finger 363, carrying the entire device 310, into her vagina, and with her fingertip 362 pushes the tip 328 of the device fully into the most proximal portion of her vagina, posterior to her cervix 344. Holding the device 310 in this position, the patient uses the bulb 331 to partially inflate the inflatable chamber 321. Although such partial inflation causes the external walls of the device 310 to gently grip the unlubricated vaginal epithelium 341, it is not sufficient to cause the internal walls 327, 327a, 327p to significantly grip the finger 363.

The patient will quickly learn how much inflation suffices to anchor the device within the vagina while allowing her to begin withdrawal of her finger. As the finger 363 is withdrawn, the patient progressively increases the inflation to compensate for the volume of the withdrawn portion of the finger, until eventually the device is fully inflated within the vagina as illustrated in FIG. 10.

It is to be understood that all of the foregoing detailed descriptions are by way of example only, and not to be taken as limiting the scope of my invention—which is expressed only in the appended claims.

I claim:

1. A device for relieving or diagnosing incontinence in a women, comprising:
   an inflatable elongate body having proximal and distal ends that is very generally shaped and sized for insertion into such woman's vagina, the proximal end being adapted to be placed adjacent to such woman's cervix; and
   means, permanently attached to the elongate body, for adjustably inflating the elongate body and for sealing it to maintain the inflation over at least many hours so as to:
   laterally engage the vagina to retain the elongate body therein for at least many hours, and
   longitudinally distend the vagina and with it such woman's urethra;

the elongate body having, at least when inflated within the vagina, indentation means for receiving such woman's cervix while the elongate body extends into and distends the most proximal portion of the vagina posterior to the cervix;

the indentation means being being disposed near the proximal end of the elongate body, facing generally proximally, and sized to receive such woman's cervix; and the inflating and sealing means being adapted for such womans to carry, in or near her vagina and attached to the elongate body, while she pursues normal daily activities;

whereby the urethra is elongated, and such woman's bladder neck and proximal portion of the urethra are moved toward normal intraabdominal positions, when the device is inflated within the vagina.

2. The device of claim 1, wherein:

the elongate body also has, at least when inflated within the vagina, at least a slight lateral enlargement which fits just above such woman's levator ani sling to help retain the elongate body within the vagina.

3. The device of claim 2, wherein:

the lateral enlargement is also inflatable to engage the levator ani sling to facilitate retention of the elongate body within the vagina.

4. The device of claim 3, wherein:

the lateral enlargement and the elongate body together form a substantially unitary inflatable chamber for inflation through the inflating and sealing means.

5. The device of claim 1, wherein the elongate body, when within the vagina, has an end that is distal with respect to the vagina; and the inflation means comprise:

a flexible airtight chamber within the elongate body; and a valve and fitting therein for use in inflating or deflating the chamber;

the valve being manually operable from the distal end of the elongate body while the elongate body is within the vagina.

6. The device of claim 5, wherein:

the fitting is accessible at the distal end of the elongate body for attachment of a source of compressed gas, while the elongate body is within the vagina.

7. The device of claim 5, also comprising:

means for facilitating stiffening of the elongate body while it is deflated, to facilitate insertion into the vagina.

8. The device of claim 5, wherein:

the elongate body also has, at least when inflated within the vagina, at least a slight lateral enlargement which fits just above such woman's levator ani sling to help retain the elongate body within the vagina.

9. The device of claim 8, wherein:

the lateral enlargement is also inflatable to engage the levator ani sling to facilitate retention of the elongate body within the vagina.

10. The device of claim 9, wherein:

the lateral enlargement and the elongate body together form a substantially unitary inflatable chamber for inflation through the inflating and sealing means.

11. The device of claim 1, also comprising:

means for facilitating stiffening of the elongate body while it is deflated, to facilitate insertion into the vagina.

12. The device of claim 11 wherein:

the facilitating means comprise a longitudinal cavity that is formed within the elongate body, open at the distal end of the elongate body, extending near the proximal end of the elongate body, and adapted to receive one of such woman's fingers to push the elongate body into the vagina.

13. The device of claim 12, wherein:

the elongate body also has, at least when inflated within the vagina, at least a slight lateral enlargement which fits just above such woman's levator ani sling to help retain the elongate body within the vagina.

14. The device of claim 13, wherein:

the lateral enlargement is also inflatable to engage the levator ani sling to facilitate retention of the elongate body within the vagina.

15. The device of claim 14, wherein:

the lateral enlargement and the elongate body together form a substantially unitary inflatable chamber for inflation through the inflating and sealing means.

16. The device of claim 1, wherein:

the inflation means terminate in fitting means for attachment of a separate pneumatic inflation bulb.

17. The device of claim 1:

wherein the inflation means terminate in fitting means for attachment of a separate pneumatic inflation device; and having an outer surface that is free of button-like electrical contacts.

18. The device of claim 1, wherein:

the device is sized so that when inflated within the vagina it elongates the urethra, and moves the bladder neck and proximal portion of the urethra toward normal intraabdominal positions, by an amount that is generally sufficient to render the urethra capable of withstanding bladder pressures characteristic of anatomical incontinence;

whereby the device when inflated within the vagina relieves symptoms of anatomical incontinence.

19. The device of claim 18, wherein:

the device is sized so that when inflated within the vagina it elongates the urethra, and moves the bladder neck and proximal portion of the urethra toward normal intraabdominal positions, by an amount that is generally insufficient to render the urethra capable of withstanding bladder pressures characteristic of bladder instability;

whereby the device facilitates diagnostic distinction between anatomical incontinence and bladder instability.

20. The device of claim 19, wherein:

the elongate body also has, at least when inflated within the vagina, at least a slight lateral enlargement which fits just above such woman's levator ani sling to help retain the elongate body within the vagina.

21. The device of claim 20, wherein:

the lateral enlargement is also inflatable to engage the levator ani sling to facilitate retention of the elongate body within the vagina.

22. The device of claim 21, wherein:

the lateral enlargement and the elongate body together form a substantially unitary inflatable chamber for inflation through the inflating and sealing means.

23. The device of claim 18, wherein:
the elongate body also has, at least when inflated within the vagina, at least a slight lateral enlargement which fits just above such woman's levator ani sling to help retain the elongate body within the vagina.

24. The device of claim 23, wherein:
the lateral enlargement is also inflatable to engage the levator ani sling to facilitate retention of the elongate body within the vagina.

25. The device of claim 24, wherein:
the lateral enlargement and the elongate body together form a substantially unitary inflatable chamber for inflation through the inflating and sealing means.

26. The device of claim 1, wherein:
the elongate body is adapted for insertion by such woman herself and is wholly flexible.

27. The device of claim 1, wherein:
the indentation is off-center of the proximal end of the enlongate body, anteriorly with respect to such woman's vagina when the elongate body is inserted therein.

28. The device of claim 1, wherein:
the inflating and sealing means are permanently attached to the distal end of the elongate body.

29. A method for relieving or diagnosing incontinence in a woman, comprising the steps of:
inserting into such woman's vagina an inflatable elongate body that is very generally shaped and sized to fit within the vagina, and that has, at least when inflated within the vagina, an indentation near the proximal end of the elongate body to receive such woman's cervix while the elongate body extends into and distends the most proximal portion of the vagina posterior to the cervix;
said inserting step including orienting the elongate body so that at least upon inflation thereof the indentation will receive such woman's cervix while the elongate body extends into and distends the most proximal portion of the vagina posterior to the cervix;
then adjustably inflating the elongate body while maintaining the orientation thereof so that the indentation receives such woman's cervix while the elongate body extends into and distends the most proximal portion of the vagina posterior to the cervix;
sealing the elongate body to maintain the inflation over at least many hours, so that the elongate body:
laterally engages the vagina to retain the elongate body therein, and
longitudinally distends the vagina and with it such woman's urethra, and
moves such woman's bladder neck and proximal portion of her urethra toward normal intraabdominal positions; and
then leaving the elongate body so inflated within the vagina over at least many hours.

30. The method of claim 29, wherein:
the elongate body also has, at least when inflated within the vagina, at least a slight lateral enlargement which fits just above such woman's levator ani sling to help retain the elongate body within the vagina;
the inserting step further includes positioning the lateral enlargement above the levator ani sling; and
the inflating step comprises maintaining the lateral enlargement above the levator ani sling.

31. A method for relieving or diagnosing incontinence in a woman, comprising the steps of:
inserting into such woman's vagina an inflatable elongate body that is very generally shaped and sized to fit within the vagina, and that has, at least when inflated within the vagina:
an indentation near the proximal end of the elongate body to receive such woman's cervix while the elongate body extends into and distends the most proximal portion of the vagina posterior to the cervix, and
at least a slight lateral enlargement which fits just above such woman's levator ani sling to help retain the elongate body within the vagina;
then adjustably inflating the elongate body; and inflating the lateral enlargement to engage the levator ani sling, thereby facilitating retention of the elongate body within the vagina;
sealing the elongate body to maintain the inflation over at least many hours, so that the elongate body:
laterally engages the vagina to retain the elongate body therein, and
longitudinally distends the vagina and with it such woman's urethra, and
moves such woman's bladder neck and proximal portion of her urethra toward normal intraabdominal positions; and
then leaving the elongate body and lateral enlargement so inflated within the vagina over at least many hours.

32. The method of claim 31, wherein:
the lateral enlargement and the elongate body together form a substantially unitary inflatable chamber for inflation together in a single inflating step; and
the inflating step comprises inflating the unitary chamber to inflate the lateral enlargement and the elongate body together in a single step.

33. A method for relieving or diagnosing incontinence in a woman, comprising the steps of:
inserting into such woman's vagina an inflatable elongate body that is very generally shaped and sized to fit within the vagina, and that has, at least when inflated within the vagina, an indentation near the proximal end of the elongate body to receive such woman's cervix while the elongate body extends into and distends the most proximal portion of the vagina posterior to the cervix;
then adjustably inflating the elongate body;
sealing the elongate body to maintain the inflation over at least many hours, so that the elongate body:
laterally engages the vagina to retain the elongate body therein, and
longitudinally distends the vagina and with it such woman's urethra, and
moves such woman's bladder neck and proximal portion of her urethra toward normal intraabdominal positions; and
then leaving the elongate body so inflated within the vagina over at least many hours; and wherein:
the elongate body and a valve and fitting attached thereto for use in inflating or deflating the chamber, said valve being manually operable from the distal end of the elongate body while the elongate body is within the vagina; and the inflating step comprises affixing to the valve and fitting a source of compressed gas, while the elongate body is within the vagina, and supplying such gas from such source through the valve and fitting into the elongate body.

34. A method for relieving or diagnosing incontinence in a woman, comprising the steps of:

inserting into such woman's vagina an inflatable elongate body that is very generally shaped and sized to fit within the vagina, and that has, at least when infalted within the vagina, an indentation near the proximal end of the elongate body to receive such woman's cervix while the elongaqe body extends into and distends the most proximal portion of the vagina posterior to the cervix;

then adjustably inflating the elongate body;

before or during the insertion step, or both, stiffening the elongate body while it is at least mostly deflated, to facilitate the insertion step;

sealing the elongate body to maintain the inflation over at least many hours, so that the elongate body:

laterally engages the vagina to retain the elongate body therein, and longitudinally distends the vagina and with it such woman's urethra, and moves such woman's bladder neck and proximal portion of her urethra toward normal intraabdominal positions; and then leaving the elongate body so inflated within the vagina over at least many hours.

35. The method of claim 34, wherein:

a longitudinal cavity is formed within the elongate body, open at the distal end of the elongate body and extending near the proximal end of the elongate body, and adapted to receive one of such woman's fingers to push the elongate body into the vagina; and the stiffening step comprises inserting a finger into the cavity to push the elongate body into the vagina; and all of the recited steps are performed by such woman herself.

36. A method for relieving or diagnosing incontinence in a woman, and particularly for use in diagnosing such woman's previously reported symptoms of incontinence; said method comprising the steps of:

inserting into such woman's vagina an inflatable elongate body that is very generally shaped and sized to fit within the vagina, and that has, at least when inflated within the vagina, an indentation near the proximal end of the elongate body to receive such woman's cervix while the elongate body extends into and distends the most proximal portion of the vagina posterior to the cervix;

then adjustably inflating the elongate body;

sealing the elongate body to maintain the inflation over at least many hours, so that the elongate body:

laterally engages the vagina to retain the elongate body therein, and longitudinally distends the vagina and with it such woman's urethra, and moves such woman's bladder neck and proximal portion of her urethra toward normal intraabdominal positions; and then leaving the elongate body so inflated within the vagina over at least many hours;

wherein said elongation of the urethra, and said moving of the bladder neck and proximal portion of the urethra toward normal intraabdominal positions, are generally sufficient to render the urethra capable of withstanding bladder pressures characteristic of anatomical incontinence, but not those characteristic of bladder instability; and also comprising the step of, after at least a protracted part of the leaving step, determining whether such previously reported symptoms of incontinence were relieved.

37. The method of claim 36, also comprising the step of:

diagnosing such woman's incontinence as arising from anatomical incontinence if such previously reported symptoms were relieved; and diangosing such woman's incontinence as arising from bladder instability if such previously reported symptoms were not relieved.

* * * * *